United States Patent
Jin et al.

(10) Patent No.: US 8,353,844 B2
(45) Date of Patent: Jan. 15, 2013

(54) SPIROMETRY-BASED METHOD FOR CONTINUOUS MONITORING OF WORK OF BREATHING AND MONITORING DEVICE THEREOF

(75) Inventors: Wei Jin, Shenzhen (CN); Jilun Ye, Shenzhen (CN)

(73) Assignee: Shenzhen Mindray Bio-Medical Electronics Co., Ltd, Shenzhen (CN)

( * ) Notice: Subject to any disclaimer, the term of this patent is extended or adjusted under 35 U.S.C. 154(b) by 1167 days.

(21) Appl. No.: 12/205,543

(22) Filed: Sep. 5, 2008

(65) Prior Publication Data
US 2009/0062674 A1    Mar. 5, 2009

(30) Foreign Application Priority Data
Sep. 5, 2007 (CN) .......................... 2007 1 0076886

(51) Int. Cl.
*A61B 5/08* (2006.01)
(52) U.S. Cl. ........................................................ 600/529
(58) Field of Classification Search ........................ None
See application file for complete search history.

(56) References Cited

U.S. PATENT DOCUMENTS

| | | |
|---|---|---|
| 3,703,893 A | 11/1972 | Hardway, Jr. |
| 2003/0045807 A1* | 3/2003 | Daniels et al. ................ 600/538 |

FOREIGN PATENT DOCUMENTS

| | | |
|---|---|---|
| CN | 101002972 A | 7/2007 |
| WO | 0045881 | 8/2000 |
| WO | 2004019766 A3 | 3/2004 |

* cited by examiner

*Primary Examiner* — Shanon A Foley
(74) *Attorney, Agent, or Firm* — Kory D. Christensen; Stoel Rives LLP

(57) ABSTRACT

A spirometry-based device for continuous monitoring of work of breathing (WOB) includes a flow sensor and a respiratory mechanics module connected with the flow sensor. The flow sensor may sample an airway gas flow and an airway pressure when a patient is in a state of inspiration. The respiratory mechanics module may calculate an incremental amount of a gas volume that flows to the patient side in a sampling period, calculate a product of the airway pressure and the incremental amount of the gas volume in the sampling period, and accumulate the product into the WOB.

5 Claims, 4 Drawing Sheets

SPIROMETRY-BASED METHOD FOR CONTINUOUS MONITORING OF WORK OF BREATHING AND MONITORING DEVICE THEREOF

CROSS-REFERENCE TO RELATED APPLICATIONS

This application claims priority to Chinese Patent Application No. 200710076886.8, filed on Sep. 5, 2007, for "Spirometry-Based Method for Continuous Monitoring of Work of Breathing," the disclosure of which is fully incorporated herein by reference.

TECHNICAL FIELD

The present disclosure relates generally to a technique for monitoring respiratory parameters, and more particularly, to a method and device for monitoring spirometry parameters of a patient under care.

BRIEF SUMMARY

A spirometry-based method and device are disclosed for continuous monitoring of work of breathing (WOB).

DETAILED DESCRIPTION

Figure 1:
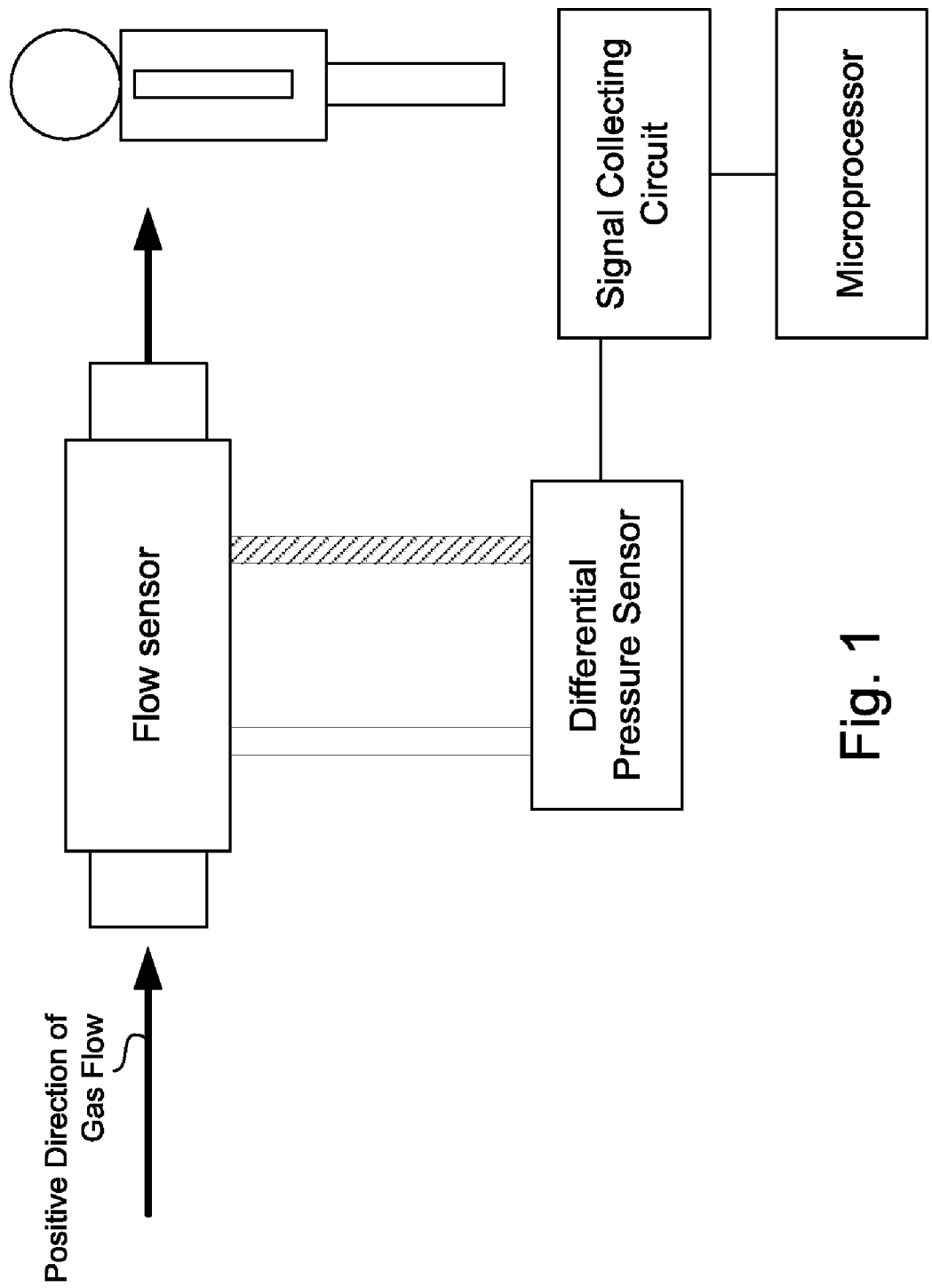
FIG. 1 is a schematic diagram of a device to continuously monitor work of breathing (WOB)

In the monitoring of respiratory mechanics, work of breathing (WOB) is of great clinical significance. WOB can be differentiated to two categories, namely, ventilator WOB and patient.WOB. Ventilator WOB is the work done by a ventilator so as to deliver a tidal volume into a patent's lungs under mechanical ventilation or supported respiration. Ventilator WOB reflects the status of ventilation and the level of support to the patient's respiration, where the monitored object is a ventilation device, such as an anesthesia machine or a ventilator.

Patient WOB, on the other hand, is the work done by a patient by spontaneously inhaling a certain amount of gas into his lungs during spontaneous or supported respiration with the contraction of his respiration-related muscles. In the case of patient WOB, the monitored object is the patient.

Depending on its effects, WOB is divided into two parts, namely, elastic WOB and non-elastic WOB. Elastic WOB refers to the work done by a ventilator or a patient against the elasticity of the respiration system, whereas non-elastic WOB refers to work done by a ventilator or a patient against the resistance (non-elastic) imposed on the gas flow by the pneumatic system, which is therefore also referred to as "work of resistance."

In the state of spontaneous respiration, it is not easy to measure the elastic work of a patient in bed, as it requires measurement of the Compliance value of the lung-thorax complex, which furthermore requires the measurement of intrathoracic pressure. However, as it is very difficult to measure intrathoracic pressure directly, it is typically reflected indirectly by the measurement of esophageal pressure. Therefore, the generally so-called patient WOB does not include the elastic work done by the respiratory muscles and the diaphragm in order to overcome the compliance of the lung and the thoracic wall during spontaneous respiration, but refers to the work done by the patient's lung to the gas.

WOB is an important clinical parameter for spirometry. By the monitoring of WOB, the level of the elastic and non-elastic resistance can be evaluated so as to quantify the level of respiration difficulty of a patient. Respiration therapy is also guided on the selection of ventilation mode and related parameter settings, which may reduce the after-load and avoid respiratory muscle fatigue. The monitoring of WOB also helps in evaluating the degree of a patient's respiratory function recovery and thus guides the withdrawal of the ventilator. Moreover, it is also an important parameter to evaluate the patient-machine counteractions which is critical for the design of pneumatic block and ventilation modes of ventilators so as to make them more adaptable to human physiology and pathology.

According to the definition of WOB, the value WOB is the integral of the airway pressure P with respect to the change of volume dV in the inspiratory phase of one respiratory period, that is:

$$WOB = \int_{V=0}^{VT} P \cdot dV, \tag{1}$$

wherein VT is the tidal volume, that is, the volume at inspiration end.

There are not many devices that provide WOB measurement. Most of them are ventilators. They usually use two methodologies of approximate calculation. One uses the different values of the airway pressure during the inspiration phase and the tidal volume, that is:

Ventilator WOB=(initial inspiratory pressure+end-inspiratory pressure)×tidal volume/2 (2)

The other obtains Ventilator WOB by multiplying the average inspiratory airway pressure by the tidal volume, that is:

Ventilator WOB=average airway pressure during the inspiratory phase×tidal volume (3)

The above ventilator-based method for measuring the WOB has the following drawbacks:

1) Limitation of application. It is not applicable for non-ventilator patients, e.g., patients using anesthesia machines and patients in the spontaneous respiration.

2) As an approximated calculation WOB, the result by Formula 2 approximates to the real value but is not accurate, even based on theoretical analysis. Further, comparing Formula 3 with Formula 1, i.e., the definition formula for WOB, it can be found that the two formulae are not mutually derivable into each other. Indeed, the work of breathing is approximately calculated by multiplying the mean pressure in the inspiratory phase by the tidal volume.

3) A ventilator including such ventilating portions as airway, valves, etc., has a high cost, itself; whereas the work of breathing and other respiratory mechanics parameters can be monitored without the ventilating portions at all.

Additionally, there is a conventional method for measuring the work of breathing, i.e., the Campbell diagram measuring method, which calculates the work of breathing precisely by the pressure-volume loop and the area of the compliance curves of the lung and the thoracic wall. Although it can measure the work of breathing precisely and obtain the compliance curve of the lung and the thoracic wall by means of an invasive procedure, being based on an analysis of the diagram, this conventional method cannot achieve continuous and real-time monitoring. In a time of advanced microelectronic technologies, the conventional method is more applicable to the contrast and the verification of the results measured by a new method.

In recent years, some scholars have studied the prediction reliability concerning the success rate of ventilator withdrawal from the ventilator-dependent patients by using a metabolization monitoring technique beside the clinical bed and measuring the amount of oxygen consumption by a patient under different ventilation conditions as the index for the work of breathing. However, the metabolization monitoring technique can only be used to monitor the work of breathing done by the patient, rather than the work done by the ventilator or the anesthesia machine in the case of mechanical respiration. Although the human body metabolization or the patient's oxygen consumption amount can indicate the energy consumption for the work done by the patient, it can not be guaranteed that all the energy is consumed by the patient for the work of breathing. For example, the amount of oxygen consumption may also increase when the patient exercises or tenses up. Therefore, one limitation of the method lies in its great susceptibility to disturbance, which results in a rather narrow range of application.

What is needed is a method and device for overcoming the deficiencies of conventional methods and devices that is stable, highly precise, easy to operate, and widely used. To this end, the present disclosure provides a spirometry-based method for continuous monitoring of work of breathing in a system having the respiratory mechanics module. The method may include sampling an airway gas flow and airway pressure at a certain sample rate by the respiratory mechanics module when a patient side of the system is in a state of inspiration such that the system obtains an incremental amount of a gas volume that flows into the patient during the sampling interval $\Delta t$. The method may further include calculating a product of the airway pressure and the incremental amount of the gas volume in the sampling period. The method may also include accumulating the product into the work of breathing WOB.

In the above spirometry-based method for continuous monitoring of work of breathing, a system may performs the above steps circularly until the end of an inspiratory phase, wherein work of breathing WOB obtained at the end of inspiration is adopted as a present total work of breathing (WOBtot).

In the above spirometry-based method for continuous monitoring of work of breathing, the sampling step may include obtaining the gas flow through a flow sensor upon arrival of a sampling period of the respiratory mechanics module and multiplying the gas flow by the sampling period $\Delta t$ to give the incremental amount of the gas volume. Moreover, the sampling step may further include allocating a current value of the gas volume to a static variable past_volume; and adding the incremental amount of the gas volume to the current value of the gas volume to update a value of the gas volume with the sum thereof.

The above spirometry-based method for continuous monitoring of work of breathing may also include calculating elastic work by obtaining a tidal volume VT and peak inspiratory pressure PIP measured by the respiratory mechanics module under a condition of mechanical respiration to give the elastic work $WOB_{elastic}$:

$$WOB_{elastic} = \frac{1}{2} VT \cdot PIP.$$

The present disclosure provides a spirometry-based device for continuous monitoring of work of breathing. The device may include a respiratory mechanics module interconnected with a flow sensor. Gas flow and airway pressure are sampled in a sampling period by the respiratory mechanics module when a patient side of the system is in a state of inspiration; an incremental amount of a gas volume that flows to the patient during the sampling period $\Delta t$ is calculated; and a product of the airway pressure and the incremental amount of the gas volume in the sampling period is calculated, which is accumulated into the work of breathing WOB.

In the above spirometry-based device for continuous monitoring of work of breathing, the respiratory mechanics module and the flow sensor perform the above steps circularly until the end of an inspiratory phase, wherein work of breathing (WOB) obtained at the end of inspiration is adopted as a present total work of breathing (WOBtot).

In the above spirometry-based device for continuous monitoring of work of breathing, the respiratory mechanics module obtains a gas flow through a flow sensor upon arrival of a next sampling period and multiplies the airway flow by the sampling period $\Delta t$ to obtain the incremental amount of the gas volume. The respiratory mechanics module further allocates a current value of the gas volume to a static variable past_volume, and adds the incremental amount of the gas volume to the current value of the gas volume to update a value of the gas volume with the sum thereof.

The above spirometry-based device for continuous monitoring of work of breathing obtains a tidal volume VT and peak inspiratory pressure PIP measured by the respiratory mechanics module under a condition of mechanical respiration to give the elastic work $WOB_{elastic}$ as:

$$WOB_{elastic} = \frac{1}{2} VT \cdot PIP.$$

The disclosed method and device has the following advantages over conventional techniques:

1) Since the respiratory mechanics module performs real-time sampling and automatic measuring, measurement operation is easy;

2) Since the respiratory mechanics module performs measurement on the patient side, the pressure and flow values for calculating the work of breathing are relatively closer to the real conditions of the lung, increasing the accuracy of the result;

3) The method according to the present disclosure is based on the definition of work of breathing excluding any approximate estimation, which further enhances the accuracy of the result;

4) The cost of the monitoring device is greatly reduced;

5) The monitoring device is highly compatible and has a strong potential of integration; with the respiratory mechanics module as a carrier, the monitoring device can be integrated into various devices, including vital signs monitors, anesthesia machines, ventilators, respiration monitors, etc., after incorporation of monitoring of the work of breathing; and 6) A current value of the work of breathing can be obtained from any sampling point in an inspiratory state through real-time and continuous measurement.

Referring now to FIG. 1, a continuous monitoring device of work of breathing according to the present disclosure comprises a flow sensor and a respiratory mechanics module. In one embodiment, the respiratory mechanics module includes a differential pressure sensor, a signal collecting circuit, and a microprocessor. Real-time measurement of the relative pressure (P) and the gas flow inside the airway is performed by tandem connection of the flow sensor between the Y piece and the endotracheal tube or a respirator on the patient side, and by coordinating the flow sensor with the differential pressure sensor, while the signal collecting circuit collects and processes signals. On the other hand, the microprocessor can obtain a volume (V) of the gas that has passed the flow sensor at each moment by accumulating the products of flow and time at different moments. In addition, the tidal volume (VT) and the peak inspiratory pressure (PIP) may be obtained by monitoring the maximums of the airway pressure and the gas volume during a full respiratory cycle. Since the positive and negative directions of the gas flow indicate the Inspiratory Phase and the Expiratory Phase, respectively, the inspiratory time (Ti) may be easily measured by the timer in the microprocessor.

Figure 2:
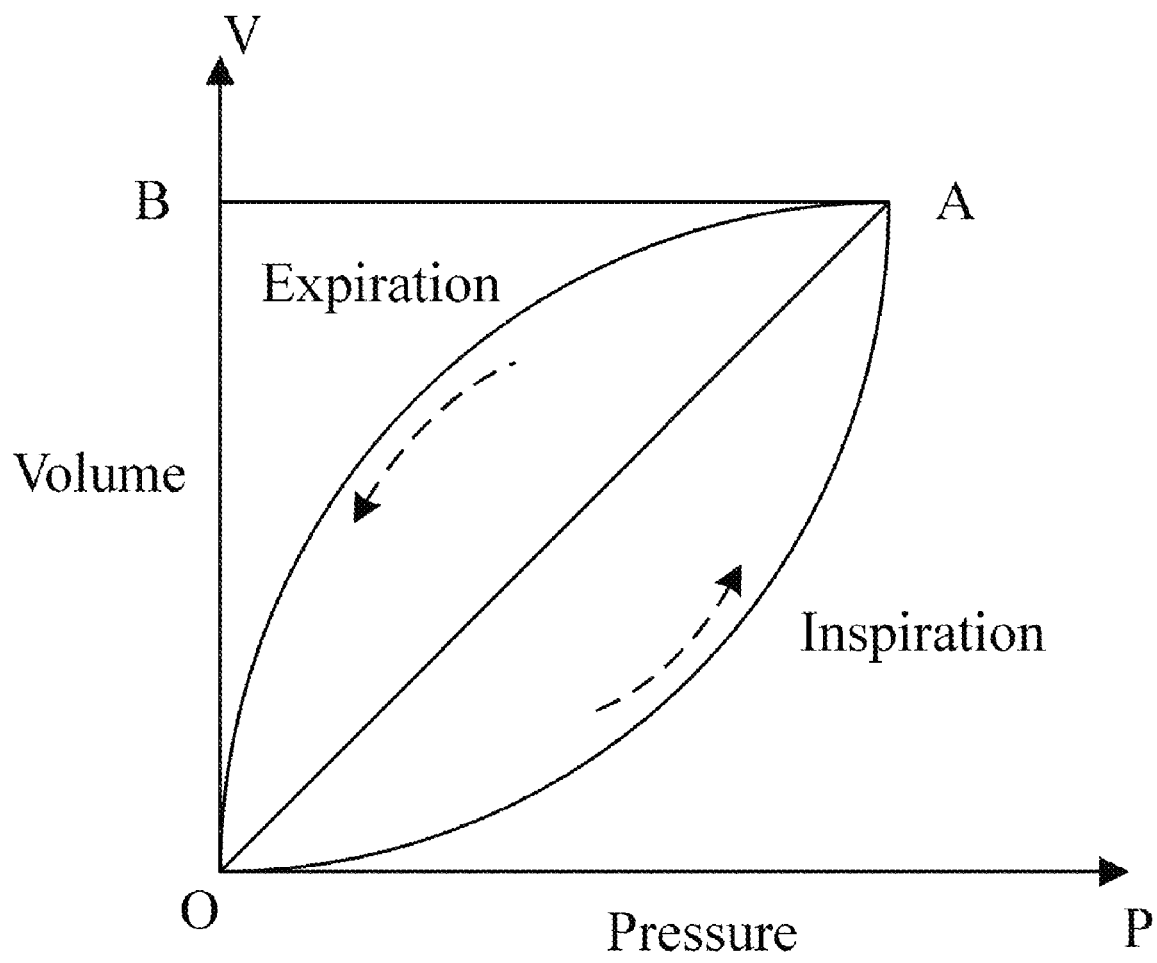
FIG. 2 is graph illustrating a pressure-volume loop of mechanical respiration.

FIG. 2 is a graph of the periodical pressure-volume loop in the airway during the mechanical respiration. Since negative pressure does not occur in the airway during normal mechanical ventilation, the respiratory loop theoretically will always be located in the first quadrant of the coordinate system. During the process of air breathing, the ventilation apparatus does work to the gas mainly against the airway resistance, the elasticity of the thoracic wall and the lung, as well as the elasticity of the air channel (in the state of positive pressure, the air channel expands under the airway pressure). According to the definition of the work of breathing, the area of the sector-like loop (the loop is irregular in a real process of respiration) OAB indicates the total work of breathing, while the area of the triangle OAB indicates the elastic work. The elastic work subtracted from the total work of breathing gives the work of resistance, that is:

$$WOB_{resist} = WOB_{tot} - WOB_{elastic}.$$

As illustrated by FIG. 2, the area of the triangle OAB can be derived from VT and PIP. That is, the elastic work is:

$$WOB_{elastic} = \frac{1}{2} VT \cdot PIP.$$

Figure 3:
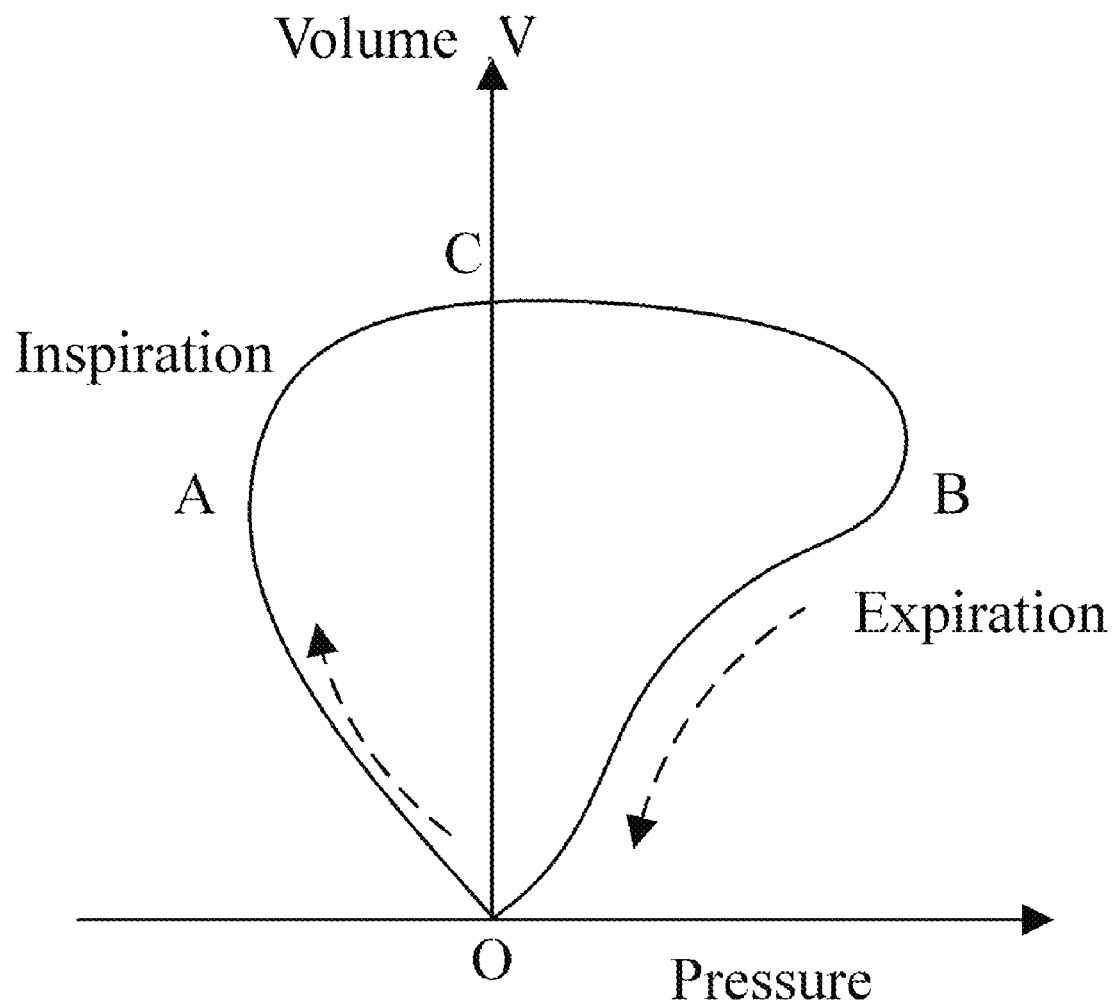
FIG. 3 is a graph illustrating a pressure-volume loop of spontaneous respiration.

FIG. 3 is a graph of the periodical pressure-volume loop in the airway during autonomous respiration. Since negative pressure occurs in the airway in the inspiratory process of autonomous respiration, the respiratory loop will theoretically span over the first and second quadrants. During autonomous respiration, work is mainly done by the lungs of the patient against the airway resistance, and there hardly exists elastic work done against the elasticity of the airway. In this case, it makes no sense clinically to measure the elastic work. Accordingly, the elastic work may be ignored where the airway is not occluded. That is, the area enclosed by the curve OAC indicates the work of breathing (work of resistance).

The volume (V) of the gas inhaled by the patient varies with time during the process of respiration, which gives $$V = V(t).$$

Assuming that P is the function of V, that is, P=P(V), in the diagram of the volume-pressure loop, while V varies with time, P also varies with time, which gives:

$$P(V) = P(V(t)).$$

Assuming P'(t)=P(V(t)) from the definition formula for WOB(formula 1), the total work of breathing may be derived as:

$$WOB_{tot} = \int_{V=0}^{VT} P(V(t)) \cdot dV(t) = \int_{t=0}^{Ti} P'(t) \cdot dV(t), \quad (4)$$

wherein Ti is the end-inspiratory time (value of t).

During airway monitoring based on the respiratory mechanics module, the sampling of P and V by the microprocessor is discrete. Assuming the sampling frequency thereof is f, the respiratory mechanics module obtains P and V value sequences at the interval of 1/f from the sampling process, that is:

$$P_n = P'(n/f), V_n = V(n/f), n=0, 1, 2, 3 \ldots;$$

with reference to the formula 4, the discrete algorithm for calculating the total work of breathing may be derived to be:

$$WOB_{tot} = \sum_{n=1}^{Ti \cdot f} P_n \Delta V = \sum_{n=1}^{Ti \cdot f} P_n [V_n - V_{n-1}]; \quad (5)$$

wherein, Ti, Pn, Vn are obtained from the measurement by the respiratory mechanics module since f is already known. Formula 5 serves as the theoretical basis for work of breathing monitored by the respiratory mechanics module.

According to the discrete algorithm for calculating the total work of breathing, the microprocessor for calculating the work of breathing defines the automatic variables of volume, WOB, press and flow, to be allocated with the gas volume, the work of breathing, the airway pressure and the airway flow in the airway at a certain moment respectively.

Figure 4:
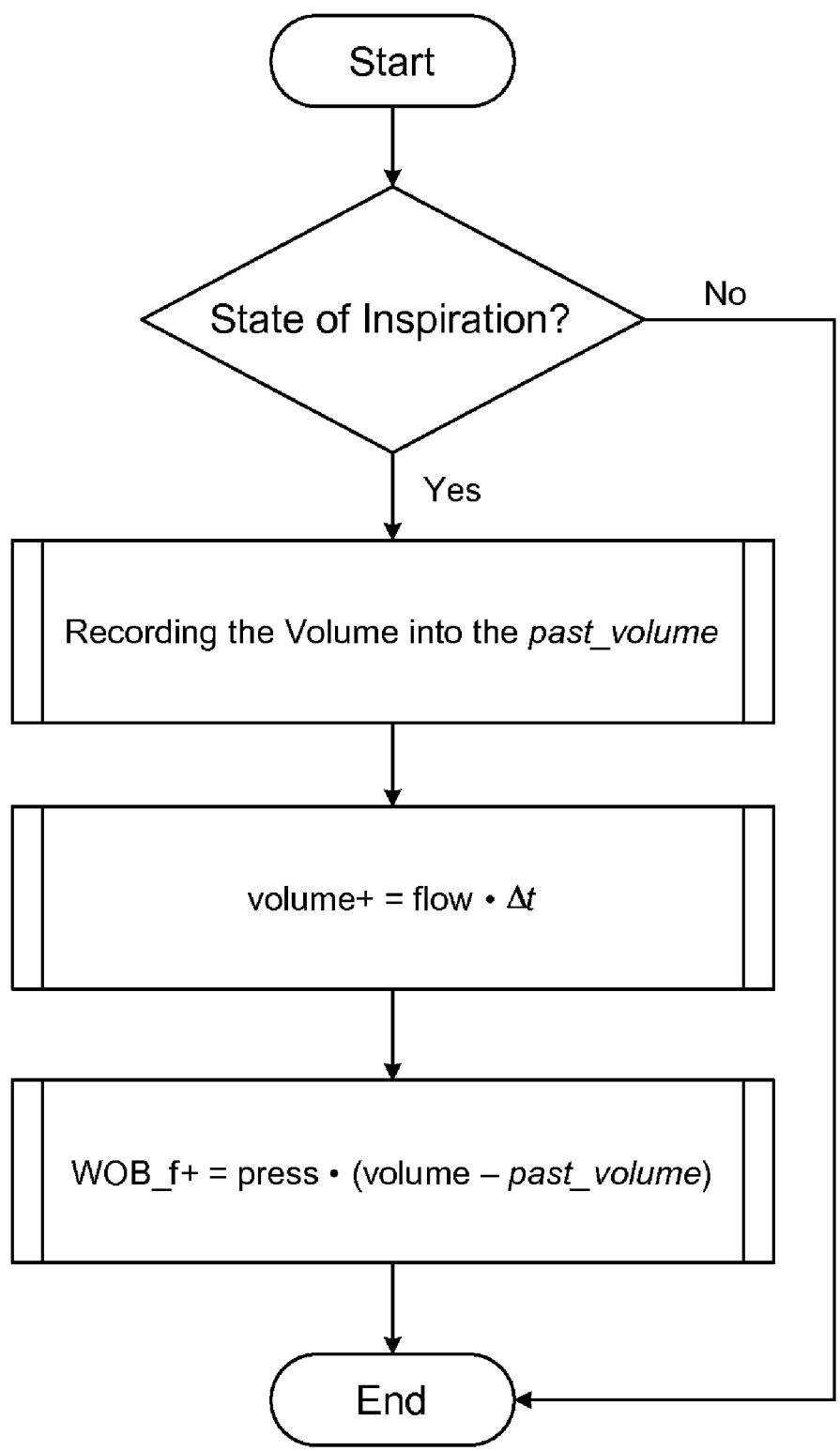
FIG. 4 is an exemplary flow chart of a method for measuring WOB.

FIG. 4 is a flowchart for a method for measuring the work of breathing. As shown in FIG. 4, the method for judging whether it is the inspiratory state of a respiratory period is performed by checking whether the sign "flow" of the airwayflow is positive. In one embodiment, a static variable past_volume is defined, which is initialized to be 0; in the inspiratory state, the current value of "volume" is loaded into past_volume; and upon arrival of the next sampling point of the respiratory mechanics module, the volume of the gas passing the sensor within time period Δt is obtained by multiplying "flow" by the sampling period Δt, which is added to the current value of "volume", with the sum thereof being loaded into "volume" for updating "volume". For example, if the sampling frequency is 100 Hz, then Δt=0.01 s, such that volume-past-volume corresponds to Vn−Vn−1 in Formula 5. The press*(volume-past_volume) calculated for each sampling is accumulated to be loaded into WOB until the end of the inspiratory phase. Then the WOB obtained at the end of inspiration is the total work of breathing. In one embodiment, a WOB obtained after completion of each respiratory period is counted as the total work of breathing of the present respiration.

Under the condition of mechanical respiration, the elastic work may be calculated with VT and PIP obtained upon completion of the respiratory period, so as to further achieve the value of the work of resistance.

Detailed descriptions of several example embodiments are provided above. However, the invention is not restricted to these example embodiments. Without departing from the scope of the invention, those skilled in this art may make changes and modifications, which will all fall into the claims of the invention.

Furthermore, the described features, operations, or characteristics may be combined in any suitable manner in one or more embodiments. It will also be readily understood that the order of the steps or actions of the methods described in connection with the embodiments disclosed may be changed as would be apparent to those skilled in the art. Thus, any order in the drawings or Detailed Description is for illustrative purposes only and is not meant to imply a required order, unless specified to require an order.

Embodiments may include various steps, which may be embodied in machine-executable instructions to be executed by a general-purpose or special-purpose computer (or other electronic device). Alternatively, the steps may be performed by hardware components that include specific logic for performing the steps or by a combination of hardware, software, and/or firmware.

Embodiments may also be provided as a computer program product including a machine-readable medium having stored thereon instructions that may be used to program a computer (or other electronic device) to perform processes described herein. The machine-readable medium may include, but is not limited to, hard drives, floppy diskettes, optical disks, CD-ROMs, DVD-ROMs, ROMs, RAMs, EPROMs, EEPROMs, magnetic or optical cards, solid-state memory devices, or other types of media/machine-readable medium suitable for storing electronic instructions.

As used herein, a software module or component may include any type of computer instruction or computer executable code located within a memory device and/or transmitted as electronic signals over a system bus or wired or wireless network. A software module may, for instance, comprise one or more physical or logical blocks of computer instructions, which may be organized as a routine, program, object, component, data structure, etc., that performs one or more tasks or implements particular abstract data types.

In certain embodiments, a particular software module may comprise disparate instructions stored in different locations of a memory device, which together implement the described functionality of the module. Indeed, a module may comprise a single instruction or many instructions, and may be distributed over several different code segments, among different programs, and across several memory devices. Some embodiments may be practiced in a distributed computing environment where tasks are performed by a remote processing device linked through a communications network. In a distributed computing environment, software modules may be located in local and/or remote memory storage devices. In addition, data being tied or rendered together in a database record may be resident in the same memory device, or across several memory devices, and may be linked together in fields of a record in a database across a network.

What is claimed is:

1. A spirometry-based device for continuous monitoring of work of breathing (WOB), comprising:
   a flow sensor; and
   a respiratory mechanics module connected with the flow sensor;
   wherein the flow sensor samples an airway gas flow and an airway pressure when a patient is in a state of inspiration;
   wherein the respiratory mechanics module calculates an incremental amount of a gas volume that flows to the patient side of the flow sensor in a sampling period, calculates a product of the airway pressure and the incremental amount of the gas volume in the sampling period, and accumulates the product into the total work of breathin (WOB$_{tot}$)
   wherein the respiratory mechanics module further measures a peak inspiratory pressure (PIP) and a tidal volume (VT) under a condition of mechanical respiration and calculates elastic work of breathing (WOB$_{elastic}$) as:

$$WOB_{elastic} = \frac{1}{2} VT \cdot PIP.$$

2. The device according to claim 1, wherein the respiratory mechanics module and the flow sensor perform the following steps circularly until the end of an inspiratory phase:
   sampling a gas flow and airway pressure in a sampling period by the flow sensor when the patient is in a state of inspiration;
   calculating an incremental amount of a gas volume that flows to the patient side of the flow sensor in the sampling period;
   calculating a product of the airway pressure and the incremental amount of the gas volume in the sampling period; and
   accumulating the product into the WOB;
   wherein the WOB obtained at the end of inspiration is adopted as a present total work of breathing (WOB$_{tot}$).

3. The device according to claim 2, wherein the respiratory mechanics module obtains a gas flow through the flow sensor upon the arrival of a next sampling period; and the respiratory mechanics module multiplies the gas flow by the sampling period to obtain the incremental amount of the gas volume.

4. The device according to claim 2, wherein the respiratory mechanics module maintains a current value of the gas volume, and adds the incremental amount of the gas volume to the current value to update the value of the gas volume with the sum thereof.

5. The device according to claim 1, wherein the respiratory mechanics module further calculates a work of resistance (WOB$_{resist}$) as:

WOB$_{resist}$=WOB$_{tot}$−WOB$_{elastic}$.

* * * * *